United States Patent [19]
Butcher et al.

[11] Patent Number: 5,623,091
[45] Date of Patent: *Apr. 22, 1997

[54] PROCESS FOR THE PRODUCTION OF BIS(FLUOROMETHYL)ETHER

[75] Inventors: Jane L. Butcher, Runcorn; Thomas A. Ryan, Kelsall; Leslie Burgess, Runcorn, all of England

[73] Assignee: Imperial Chemical Industries PLC, London, England

[*] Notice: The term of this patent shall not extend beyond the expiration date of Pat. No. 5,344,998.

[21] Appl. No.: 523,194

[22] Filed: Sep. 5, 1995

Related U.S. Application Data

[62] Division of Ser. No. 268,659, Jun. 29, 1994, Pat. No. 5,463,139, which is a continuation of Ser. No. 24,255, Mar. 1, 1993, abandoned, which is a division of Ser. No. 898,786, Jun. 15, 1992, abandoned.

[30] Foreign Application Priority Data

| Jun. 14, 1991 | [GB] | United Kingdom | 9112817 |
| Jun. 14, 1991 | [GB] | United Kingdom | 9112860 |
| Jun. 14, 1991 | [GB] | United Kingdom | 9112861 |
| Nov. 13, 1991 | [GB] | United Kingdom | 9124087 |
| Dec. 11, 1991 | [GB] | United Kingdom | 9126330 |

[51] Int. Cl.$^6$ .......................... C07C 41/22; C07C 41/42
[52] U.S. Cl. .......................................................... 568/683
[58] Field of Search ............................ 568/613, 683; 570/142

[56] References Cited

U.S. PATENT DOCUMENTS

| 3,377,394 | 4/1968 | Boudakian et al. | |
| 5,344,998 | 9/1994 | Martin et al. | 568/683 |
| 5,386,064 | 1/1995 | Woodcock et al. | 568/683 |
| 5,446,215 | 8/1995 | Cook et al. | 570/142 |
| 5,463,139 | 10/1995 | Butcher et al. | 568/683 |

FOREIGN PATENT DOCUMENTS

| 1025856 | 3/1958 | Germany . |
| 2126216 | 3/1984 | United Kingdom . |

OTHER PUBLICATIONS

Weinmayr, Viktor, Hydrogen Fluoride as a Condensing Agent, VI. Reactions of Fluoroolefins with Formaldehyde in Hydrogen Fluoride, Journal of Org. Chem., vol. 28, Feb. 1963, pp. 492–494.

Sokol'skii, G.A., Fluoromethyl Esters of Sulfuric Acid, VII. Stability of Difluoromethyl Esters of Fluorosulfonic and Alkylsulfuric Acids, Translated from Zhurnal Obshchei Khimii, vol. 32, No. 4, pp. 1310–1314, Apr. 1962.

Darragh et al., Journal of Inorganic Nucl. Chemistry, 1970, vol. 32, pp. 1745–1747.

Hasek et al., J.A.C.S., vol. 82, pp. 543–551 (1913).

*Primary Examiner*—Harvey E. Behrend
*Assistant Examiner*—John R. Hardee
*Attorney, Agent, or Firm*—Cushman Darby & Cushman IP Group Pillsbury Madison & Sutro LLP

[57] ABSTRACT

A composition comprising bis(fluoromethyl)ether and less than an equimolar amount of water, a process for the production of the composition comprising contacting formaldehyde with hydrogen fluoride and separating at least some of the by-product water from bis(fluoromethyl)ether, and use of the composition for the production of difluoromethane.

8 Claims, No Drawings

PROCESS FOR THE PRODUCTION OF BIS(FLUOROMETHYL)ETHER

This is a division of application Ser. No. 8/268,659, filed Jun. 29, 1994, now U.S. Pat. No. 5,463,139, which is a continuation of Ser. No. 08/024,255 filed Mar. 1, 1993, now abandoned; which is a divisional of Ser. No. 07/898,786 filed Jun. 15, 1992, now abandoned.

This invention relates to bis(fluoromethyl)ether compositions, a process for the production of the bis(fluoromethyl)ether compositions, and to a process for the production of difluoromethane from the bis(fluoromethyl)ether compositions.

In recent years chlorofluorocarbons, which are used on a large scale around the world, have been perceived as having an adverse effect on the ozone layer and/or as contributing to global warming. Chlorofluorocarbons are used, for example, as refrigerants, as foam blowing agents, as cleaning solvents and as propellants for aerosol sprays in which the variety of applications is virtually unlimited. Consequently, much effort is being devoted to finding suitable replacements for chlorofluorocarbons which will perform satisfactorily in the many applications in which chlorofluorocarbons are used but which will not have the aforementioned environmentally harmful effects. One approach in the search for suitable replacements has centred on fluorocarbons which do not contain chlorine but which may contain hydrogen. The hydrofluorocarbon difluoromethane, also known as HFA 32, is of interest as one such replacement, in particular as a replacement in refrigeration, air-conditioning and other applications.

Several methods for the production of difluoromethane are known but many of these methods involve the use of chlorine-containing starting materials and the production of chlorine-containing by-products. Chlorine-free processes are also known and one of these, the reaction between formaldehyde and hydrogen fluoride at an elevated temperature in the presence of a fluorine-containing inorganic acid, a metal fluoride, a metal oxide or a metal chromite, has been described in U.S. Pat. No. 3,377,394. The highest yield of difluoromethane reported from this reaction is 4.2%, the major product being methyl fluoride.

The present invention resides in our finding that certain bis(fluoromethyl)ether compositions are particularly useful as starting materials for the production of difluoromethane, and that such bis(fluoromethyl)ether compositions may be readily produced.

According to a first aspect of the present invention there is provided a composition comprising bis(fluoromethyl)ether and wherein the composition comprises less than an equimolar amount of water relative to bis(fluoromethyl)ether.

We have found that such bis(fluoromethyl)ether compositions may be simply converted to difluoromethane with high yields of difluoromethane and without the production of any significant amounts of any toxic by-products.

Generally we prefer that the composition comprises as small an amount of water as possible, and the molar ratio of bis(fluoromethyl)ether to water in the composition is usually at least 2:1, preferably at least 10:1, more preferably at least 20:1 and especially at least 50:1. Optimum yields of difluoromethane are achieved using compositions substantially free from water.

Other materials, for example unreacted starting materials from which the bis(fluoromethyl)ether has been produced and other by-products, may be present in the composition, but overall the bis(fluoromethyl)ether composition may comprise at least 20 mole % bis(fluoromethyl)ether, preferably at least 35 mole % bis(fluoromethyl)ether, more preferably at least 50 mole %, particularly preferably at least 70 mole % bis(fluoromethyl)ether, and especially at least 90 mole % bis(fluoromethyl)ether.

Processes are known for the production of bis(fluoromethyl)ether, molecular formula $FH_2COCH_2F$, all of which however result in compositions comprising substantial amounts of water and other by-products. Furthermore, The bis(fluoromethyl)ether compositions of the invention may be prepared by any one of these known routes, for example by reaction of α-polyoxymethylene, $(CH_2O)_n$, with sulphur tetrafluoride as described in The Journal of Inorganic Nuclear Chemistry-32, (1970), 1748, or by reaction of trioxane with sulphur tetrafluoride as described in The Journal of the American Chemical Society 82 (1960) 543 or by reacting paraformaldehyde with hydrogen fluoride in the liquid phase in the absence of a catalyst as described in The Journal of Organic Chemistry, 28, 492(1963), so long as steps are taken to ensure that the bis(fluoromethyl)ether compositions which are produced comprise at least less moles of water than bis(fluoromethyl)ether, and preferably at least 20 mole % bis(fluoromethyl)ether.

However, many of these routes employ highly toxic and expensive starting materials and they are not suitable for the large scale manufacture of bis(fluoromethyl)ether. Preferably therefore, the bis(fluoromethyl)ether composition of the invention is prepared by contacting formaldehyde with hydrogen fluoride in the liquid phase, or in the vapour phase in the presence of a catalyst such as an activated carbon. The activated carbon may also be charged with, for example a metal fluoride such as potassium or caesium fluoride.

According to a second aspect of the invention there is provided a process for the production of bis(fluoromethyl)ether which comprises contacting formaldehyde with hydrogen fluoride and separating at least a part of the by-product water from the bis(fluoromethyl)ether produced.

We especially prefer to react formaldehyde with liquid hydrogen fluoride; this reaction may be effected simply by dissolving formaldehyde in liquid hydrogen fluoride under conditions of temperature and pressure whereby hydrogen fluoride is in the liquid phase. The reaction may be conveniently effected at about ambient temperature and pressure although temperatures above or below ambient and superatmospheric or subatmospheric pressures may be employed provided that hydrogen fluoride is in the liquid phase.

The formaldehyde may be provided in any of its known forms, for example in one of its polymeric forms, paraformaldehyde or trioxane, or in its monomeric form which may be provided, for example, from a process stream in which it has been freshly made, for example by oxidation of methanol. Accordingly, whenever used herein, the term "formaldehyde" is to be understood as including not only the monomer but also the various polymeric forms, which may be provided, for example in the form of aqueous solutions. In general, a polymeric form of formaldehyde such as paraformaldehyde is preferred where the formaldehyde is dissolved in liquid hydrogen fluoride to form bis(fluoromethyl)ether.

Paraformaldehyde and trioxane dissolve readily in liquid hydrogen fluoride and the production of bis(fluoromethyl) ether may be conveniently carried out by dissolving paraformaldehyde or trioxane in liquid hydrogen fluoride at about room temperature and at about atmospheric pressure. The invention will be described hereafter with reference to bis(fluoromethyl)ether which is produced in this way although the invention is not limited thereto.

The molar ratio of formaldehyde to hydrogen fluoride may vary considerably, for example in the range about 1:0.5 to 1:50 but in general a stoichiometric excess of hydrogen fluoride is preferred. Typically, the molar ratio of formaldehyde to hydrogen fluoride will be in the range about 1:2 to about 1:10.

Formaldehyde and hydrogen fluoride react together in the liquid phase to produce bis(fluoromethyl)ether and water according to the equation:

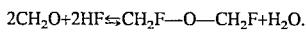

$$2CH_2O + 2HF \rightleftharpoons CH_2F-O-CH_2F + H_2O.$$

The product is therefore a mixture of unreacted hydrogen fluoride and formaldehyde, water and bis(fluoromethyl)ether. We have discovered that it is essential, for the further treatment of the bis(fluoromethyl)ether in order to produce difluoromethane, to separate at least part of the water from the bis(fluoromethyl)ether. Thus, by "separation of at least a part of the water from bis(fluoromethyl)ether", there is meant simply that these two components of the product mixture are at least partly separated from each other without limitation to separation of the other components of the mixture. Thus for example, the water may be separated from all the other components of the mixture including bis(fluoromethyl) ether, or the bis(fluoromethyl)ether may be separated from all the other components of the mixture including water. We generally prefer that the bis(fluoromethyl)ether, and optionally hydrogen fluoride, is separated from the other components of the mixture.

Separation of the bis(fluoromethyl)ether from water may be achieved in any suitable manner, for example by vaporising the bis(fluoromethyl)ether and optionally hydrogen fluoride from the product mixture obtained by reacting formaldehyde with hydrogen fluoride, or by contacting the product mixture with a solid drying agent. Thus, for example a stream of an inert gas, for example nitrogen may be sparged through the solution of bis(fluoromethyl)ether (and any unreacted formaldehyde and by-product water) in hydrogen fluoride.

The bis(fluoromethyl)ether may be separated from the water as the reaction proceeds, or they may be separated as a subsequent step after the reaction has taken place. Thus, for example, the bis(fluoromethyl)ether may be isolated from the formaldehyde and hydrogen fluoride, from which it is produced, water and any other by-products, before the bis(fluoromethyl)ether is further treated. The bis(fluoromethyl)ether may be isolated, for example, by adding alkali to the paraformaldehyde/hydrogen fluoride liquid mixture and heating the resulting alkaline solution, for example up to about 50° C., in order to drive the bis(fluoromethyl)ether off. Alternatively the bis(fluoromethyl)ether may conveniently be isolated by contacting the product stream with water at a temperature in the range from about 50° to about 80° C. The bis(fluoromethyl) ether may then be collected in a cold trap or passed directly, after drying, to a reaction vessel or zone for conversion to difluoromethane as described hereinafter.

However, the liquid phase reaction between formaldehyde and hydrogen fluoride is equilibrium limited, there being about a 60% conversion of formaldehyde to bis(fluoromethyl)ether and water at 20° C. using a substantial excess of hydrogen fluoride to drive the equilibrium towards the products. It is desirable therefore that one or both of the products, water and bis(fluoromethyl)ether is separated from the reaction mixture as soon as possible after it is formed in order to further drive the equilibrium towards the products and force the reaction to completion, thereby achieving higher conversions of reactants to products. Furthermore, it is believed that the reaction of formaldehyde with liquid hydrogen fluoride to produce bis(fluoromethyl)ether is almost instantaneous and we prefer, in order to reduce the tendency for unwanted by-products to form, that it is the bis(fluoromethyl)ether which is continuously separated from the reaction mixture as soon as possible after it is formed.

Preferably therefore, the reaction between formaldehyde and hydrogen fluoride is conducted in a manner and using apparatus whereby the bis(fluoromethyl)ether is continually separated from water as they are formed. Thus for example, the reaction may be effected by "reactive distillation" in a distillation column in which formaldehyde and hydrogen fluoride are continuously fed to the column and in which a tops stream comprising bis(fluoromethyl)ether and hydrogen fluoride, and an aqueous bottoms fraction comprising water, water/hydrogen fluoride azeotrope and unreacted formaldehyde are continually collected from the column. Alternatively the reaction between formaldehyde and hydrogen fluoride may be conducted in the presence of a water-immiscible organic solvent for the bis(fluoromethyl)ether so that as the (bis(fluoromethyl)ether is produced, the bis(fluoromethyl)ether is extracted into the solvent. These processes are described in more detail in our co-pending UK Patent Applications Nos. 9124087.9 and 92 08769.1 respectively.

We have also found that bis(fluoromethyl)ether, and in particular the bis(fluoromethyl)ether compositions of the first aspect of the invention are particularly useful as starting materials for the production of difluoromethane.

According to a third aspect of the present invention there is provided a process for the production of difluoromethane which comprises feeding bis(fluoromethyl)ether to a reaction zone whereby to produce difluoromethane.

The process of the third aspect of invention may be operated to form difluoromethane with yields of at least 5%, preferably at least 20%, more preferably at least 50% and especially at least 70%, based upon the amount of bis(fluoromethyl)ether fed to the reaction zone.

Preferably the bis(fluoromethyl)ether compositions of the first aspect of the invention, that is bis(fluoromethyl)ether compositions containing less than an equimolar amount of water, are employed to effect this third aspect of the invention and more preferably the bis(fluoromethyl)ether compositions are prepared by the second aspect of the invention.

Thus, according to a first preferred embodiment of the invention there is provided a process for the production of difluoromethane which comprises (a) contacting formaldehyde with liquid hydrogen fluoride to from a product comprising bis(fluoromethyl)ether and water, (b) separating at least a part of the water from the bis(fluoromethyl)ether and (c) feeding the bis(fluoromethyl)ether to a reaction zone whereby to produce difluoromethane.

According to a second preferred embodiment of the invention there is provided a process for the production of difluoromethane which comprises (a) contacting formaldehyde with hydrogen fluoride in the vapour phase at elevated temperature in the presence of a catalyst to produce a product comprising bis(fluoromethyl)ether and water (b) separating at least a part of the water from the bis(fluoromethyl)ether and (c) feeding the bis(fluoromethyl)ether to a reaction zone whereby to produce difluoromethane.

Step (c) of these preferred embodiments of the invention, that is the third aspect of the invention, may be effected in the liquid or vapour phase. We prefer for simplicity however, that step (c) is effected in the vapour phase by heating the bis(fluoromethyl)ether to elevated temperature. Preferably therefore the bis(fluoromethyl)ether is fed to a heating zone.

The heating zone may be part of the same vessel or apparatus in which step (a) of the process of effected. Thus for example, the formaldehyde and hydrogen fluoride may be contacted in a distillation column as previously described, the bis(fluoromethyl)ether rising through the column and the water falling down the column. A heating zone may be provided towards the top of the column in which the bis(fluoromethyl)ether, separated from water, is converted to difluoromethane. Alternatively, and preferably however, in order that as complete separation as possible of water and bis(fluoromethyl)ether is achieved, steps (a) and (c) may be performed in separate reaction vessels.

In the second preferred embodiment of the invention, both of steps (a) and (c) may therefore employ elevated temperature and both may employ a catalyst so that in practice at least a part of the bis(fluoromethyl) ether produced in step (a) may be converted to difluoromethane (step c) without a change in reaction conditions. However, we have found that for optimum results different catalysts are preferred in step (a) and step (c); the process then comprises operation of step (a) using a first catalyst to produce bis(fluoromethyl)ether and difluoromethane and operation of step (c) using a second catalyst to convert unreacted bis(fluoromethyl)ether from step (a) to difluoromethane.

In the second preferred embodiment where the formaldehyde and hydrogen fluoride are reacted in the vapour phase to produce the bis(fluoromethyl)ether, the product stream from step (a) may be passed directly to the second reaction zone after separating water from the product stream from step (a), if desired together with additional hydrogen fluoride.

The bis(fluoromethyl) ether may be introduced into the heating zone in undiluted form although, depending upon the process employed for the production of the bis(fluoromethyl)ether, it may be convenient to introduce the bis(fluoromethyl) ether vapour into the heating zone in conjunction with a diluent such as an inert carrier gas, for example nitrogen.

The temperature to which the bis(fluoromethyl) ether is heated to produce difluoromethane is such that the bis(fluoromethyl)ether is in the vapour phase and the temperature will therefore be at least 80° C., preferably at least 200° C. and more preferably at least 250° C. The temperature need be no higher than about 500° C., although higher temperatures, say up to about 700° C., may be used if desired.

Heating of the bis(fluoromethyl)ether may be carried out in the presence of hydrogen fluoride vapour. The hydrogen fluoride may be used as the diluent or carrier gas with which the bis(fluoromethyl)ether is introduced into the reaction zone or the hydrogen fluoride may be introduced into the reaction zone separately.

The heating of the bis(fluoromethyl)ether to produce difluoromethane may advantageously be performed in the presence of a catalyst. The conversion of bis(fluoromethyl)ether and selectivity to difluoromethane are dependent in particular upon the choice of catalyst in the presence of which the bis(fluoromethyl)ether is heated to elevated temperature. We have found that certain catalysts promote a high degree of selectivity to difluoromethane, whilst other catalysts promote a high degree of selectivity to trifluoromethane and other catalysts yield mixtures of both difluoromethane and trifluoromethane.

The catalyst may be for example, a metal, for example an s-block metal such as calcium, a p-block metal such as aluminium, tin or antimony, an f-block metal such as lanthanum or a d-block metal such as nickel, copper, iron, manganese, cobalt and chromium or alloys thereof; a metal oxide, for example chromia or alumina, a metal fluoride, for example, aluminium, manganese or chromium fluoride, or a metal oxyfluoride, for example an oxyfluoride of one of the aforementioned metals. The metal is preferably a d- or p-block metal, oxide, fluoride or oxyfluoride thereof, and more preferably chromium, aluminium, or a Group VIIIa metal.

We have found that difluoromethane may be produced with very high selectivity where the catalyst employed is a metal selected from the group consisting of nickel, aluminium, iron or chromium and in particular where the catalyst is an alloy or mixture of at least one of these metals. We especially prefer to employ alloys comprising more than one of these metals, and the alloys may also comprise other metals, for example molybdenum. Examples of preferred alloys include Hastelloy and stainless steel; stainless steel is especially preferred.

Furthermore we prefer that these alloys are air treated prior to use, that is the alloys are heated to elevated temperature in the presence of air, for example a temperature in the range from 300° C. to 500° C. Alternatively or additionally, this catalyst pre-treatment heating may be carried out in the presence of hydrogen fluoride.

Further preferred catalysts are chromia and iron oxide, which although they may not promote as high a degree of selectivity to difluoromethane as the preferred alloys, are very robust catalysts. Chromia and iron oxide may also be given a pre-treatment prior to their use.

The catalyst may also comprise mixtures of metals, oxides, fluorides or oxyfluorides thereof, such as for example impregnated metal oxide or oxyfluorides, or simple mixtures. Thus, for example the catalyst may comprise chromia impregnated with iron, nickel or other metals or compounds thereof, for example oxides or halides thereof or the catalyst may comprise a mixture of chromia and other metal oxides, for example iron oxide.

Other catalysts may also be used which lead to the production of monofluoromethane with a high degree of selectivity, for example a catalyst comprising zinc impregnated chromia or tin fluoride.

Accordingly in a further preferred embodiment of the third aspect of the invention there is provided a process for the production of difluoromethane which comprises heating bis(fluoromethyl)ether in the vapour phase at elevated temperature in the presence of a catalyst and optionally also in the presence of hydrogen fluoride. The catalyst is preferably at least one metal, metal oxide, metal fluoride or metal oxyfluoride.

According to a still further preferred embodiment of the invention there is provided a process for the production of difluoromethane which comprises heating bis(fluoromethyl)ether in the vapour phase at elevated temperature in the presence of a catalyst comprising: (i) a metal selected from the group consisting of nickel, chromium, aluminium and iron or an alloy of at least one of these metals, or (ii) an oxide, fluoride or oxyfluoride of one of the metals or alloys defined in (i).

The temperature to which the bis(fluoromethyl)ether is heated is dependant at least to some extent on whether the heating is effected in the presence of a catalyst and/or one of the aforementioned metals or alloys. Where the heating is effected in the presence of a catalyst, the preferred temperature is dependent on the particular catalyst used; generally where a catalyst or one of the aforementioned metals or alloys is present, the temperature may not be as high as when a catalyst or one of the aforementioned metals or alloys thereof is not present.

Typically the temperature need be no higher than about 450° C. where a catalyst or one of the aforementioned metals or alloys is used in the presence of hydrogen fluoride. Thus, for example, where the heating is effected in the presence of stainless steel and hydrogen fluoride, the temperature is preferably at least about 250° C. and more preferably at least 300° C. but need be no higher than about 400° C., generally no higher than about 350° C. However, where the fluorination catalyst is chromia in the presence of hydrogen fluoride, the temperature is preferably from about 180° C. to about 320° C., more preferably from about 200° C. to about 280° C.

The process of the invention is conveniently carried out at about ambient pressure although superatmospheric or subatmospheric pressures may be used if desired. Indeed superatmospheric pressures up to about 15 bar at lower temperatures may be generally preferred since the yield of and selectivity to difluoromethane may be increased under such conditions.

After completion of the reaction, the difluoromethane may be isolated from unchanged starting materials using conventional procedures, for example distillation.

It is particularly convenient to operate the process of the invention as a continuous process wherein unchanged bis-(fluoromethyl)ether and any hydrogen fluoride present in the difluoromethane product stream are recycled to the reaction zone.

The invention is illustrated, but not limited, by the following examples.

EXAMPLE 1

Production and Isolation of BFME 114 g of anhydrous liquid hydrogen fluoride was added with cooling to 30 g of paraformaldehyde prills in a 200 cc FEP (copolymer of tetrafluoroethylene and hexafluoropropylene) flask and the solution was stirred for 12 hours at about 0° C. The solution was then added dropwise to excess of aqueous KOH solution contained in a plastic conical flask which was connected to a series of two traps, the first containing aqueous KOH solution and the second trap being empty and cooled to −78° C. for final collection of the fluoroether. After addition of the paraformaldehyde/hydrogen fluoride mixture to the aqueous KOH solution, the alkaline solution was warmed to 50° C. to drive the fluoroether through to the cool trap. 6.2 g of pure ether was collected.

EXAMPLE 2

Production and Isolation of BFME 100 ml of anhydrous liquid hydrogen fluoride was added with cooling to 21 g of solid trioxane in a 200 cc FEP (copolymer of tetrafluoroethylene and hexafluoropropylene) flask and the solution was stirred for a few minutes at room temperature. The solution was then added slowly to 700 ml of water at about 50° C. in a FEP flask which was connected to a series of traps and through which Nitrogen was continuously purged at 100 ml/minute. The first trap contained anhydrous calcium chloride to remove any traces of water from the product stream and the product stream was collected in a second trap which was cooled by a Drikold/trichloroethylene bath. The product collected in the trap was analysed by Gas Chromatography and determined to be pure bis(fluoromethyl)ether.

EXAMPLE 3

Heating BFME in Presence of Air-Treated Chromium and HF 114 g of anhydrous liquid hydrogen fluoride was added with cooling to 30 g of paraformaldehyde prills in a 200 cc FEP (copolymer of tetrafluoroethylene and hexafluoropropylene) flask and the solution was stirred for a few minutes at 10° C.

Nitrogen was bubbled through the paraformaldehyde/hydrogen fluoride liquid mixture at a flow rate of 50 $cms^3$/minute and the vapour was fed to an Inconel reactor charged with 200 g (70 $cms^3$) of air-treated chromium granules. Air-treatment was carried out by heating the chromium granules in an air stream (1.5 l/minute) for 16 hours at about 400° C.

The Inconel tube was heated to elevated temperature. The off gases were analysed by Gas Chromatography and the results are shown in Table 1.

TABLE 1

| Temp/°C. | % BFME Conversion | % Yield (moles). | | Molar Ratio |
|---|---|---|---|---|
| | | $CH_3F$ | $CH_2F_2$ | $CH_2F_2/CH_3F$ |
| 275 | 26.08 | 1.88 | 24.20 | 12.86 |
| 309 | 57.81 | 2.96 | 54.85 | 18.54 |
| 362 | 65.09 | 1.64 | 63.44 | 38.61 |
| 403 | 59.99 | 2.41 | 57.57 | 23.84 |

EXAMPLE 4

Heating BFME in Presence of Air-Treated Copper and HF

The procedure of example 3 was followed except that the Inconel tube was packed with 133.5 g (170 $cms^3$) of air-treated copper gauze. The results are shown in Table 2 in which the yields of $CH_3F$ and $CH_2F_2$ are based on the number of moles of bis(fluoromethyl)ether charged to the reactor.

TABLE 2

| Temp/°C. | % Yield | | % BFME Conversion | Molar Ratio |
|---|---|---|---|---|
| | $CH_3F$ | $CH_2F_2$ | | $CH_2F_2/CH_3F$ |
| 209 | 0.0 | 0.0 | 0.0 | — |
| 229 | 1.61 | 1.23 | 15.22 | 0.76 |
| 250 | 3.29 | 3.9 | 41.9 | 1.18 |
| 324 | 3.0 | 5.26 | 66.67 | 1.75 |

EXAMPLE 5

Heating BFME in Presence of Iron and HF

The procedure of example 3 was followed except that the Inconel tube was packed with 464 g (144 $cms^3$) of iron chips. The results are shown in Table 3, in which the yields of $CH_2F_2$ and $CH_3F$ are based on the number of moles of bis(fluoromethyl)ether charged to the reactor.

TABLE 3

| Temp/°C. | % Yield | | BFME Conversion/% | Molar Ratio CH$_2$F$_2$/CH$_3$F |
|---|---|---|---|---|
| | CH$_3$F | CH$_2$F$_2$ | | |
| 274 | 1.5 | 0.93 | 2.44 | 0.62 |
| 311 | 3.25 | 4.35 | 7.59 | 1.34 |
| 364 | 6.15 | 16.37 | 23.36 | 2.66 |
| 394 | 7.31 | 24.69 | 34.46 | 3.38 |
| 452 | 10.81 | 55.84 | 76.10 | 5.16 |

EXAMPLE 6

Heating BFME in Presence of Air-Treated Nickel and HF

The procedure of example 3 was followed except that the Inconel reactor was packed with 402 g (80 cms$^3$) of air-treated nickel balls. The results are shown in Table 4, in which the yields of CH$_2$F$_2$ and CH$_3$F are based on the number of moles of bis(fluoromethyl)ether charged to the reactor.

TABLE 4

| Temp/°C. | % Yield | | % BFME Conversion | Molar Ratio CH$_2$F$_2$/CH$_3$F |
|---|---|---|---|---|
| | CH$_3$F | CH$_2$F$_2$ | | |
| 305 | 2.62 | 2.39 | 5.01 | 0.91 |
| 334 | 3.73 | 9.56 | 13.29 | 2.57 |
| 366 | 5.83 | 23.41 | 29.24 | 4.01 |
| 399 | 6.51 | 41.47 | 47.98 | 6.37 |
| 463 | 11.92 | 55.13 | 68.73 | 4.62 |

EXAMPLE 7

Heating BFME in Presence of Air-Treated Hastelloy C and HF

The procedure of example 3 was followed except that the Inconel reactor was packed with 83.6 g (150 cms$^3$) of air-treated Hastelloy C foil pieces. The results are shown in Table 5, in which the yields of CH$_2$F$_2$ and CH$_3$F are based on the number of moles of bis(fluoromethyl)ether charged to the reactor.

TABLE 5

| Temp/°C. | % Yield | | % BFME Conversion | Molar Ratio CH$_2$F$_2$/CH$_3$F |
|---|---|---|---|---|
| | CH$_3$F | CH$_2$F$_2$ | | |
| 209 | 0.82 | 3.49 | 4.31 | 4.24 |
| 242 | 1.25 | 12.75 | 13.99 | 10.23 |
| 300 | 1.92 | 40.82 | 42.74 | 21.29 |
| 343 | 2.80 | 59.89 | 62.70 | 21.36 |
| 387 | 3.70 | 78.74 | 82.45 | 21.28 |
| 428 | 5.32 | 85.23 | 90.55 | 16.04 |
| 466 | 7.41 | 90.56 | 97.98 | 12.22 |

EXAMPLE 8

Heating BFME in Presence of Hastelloy C and HF

The procedure of example 7 was followed except that the Inconel reactor was packed with 83.6 g (150 cms$^3$) of Hastelloy C foil pieces, which had not been air-treated. The results are shown in Table 6, in which the yields of CH$_2$F$_2$ and CH$_3$F are based on the number of moles of bis(fluoromethyl)ether charged to the reactor.

TABLE 6

| Temp/°C. | % Yield | | % BFME Conversion | Molar Ratio CH$_2$F$_2$/CH$_3$F |
|---|---|---|---|---|
| | CH$_3$F | CH$_2$F$_2$ | | |
| 257 | 0.42 | 1.87 | 2.28 | 4.5 |
| 299 | 0.92 | 8.03 | 8.95 | 8.74 |
| 330 | 1.46 | 16.64 | 18.10 | 11.43 |
| 356 | 1.94 | 31.01 | 32.95 | 16.00 |
| 384 | 2.59 | 49.53 | 52.12 | 19.15 |
| 418 | 3.32 | 60.02 | 63.35 | 18.05 |
| 472 | — | 4.67 | 59.91 | 64.58 | 12.83 |

EXAMPLE 9

Heating BFME in Presence of Air-Treated Stainless Steel Grade 304 Mesh and HF

The procedure of example 3 was followed except that the Inconel reactor was packed with 82.8 g (200 cms$^3$) of air-treated stainless steel grade 304 mesh. The results are shown in Table 7, in which the yields of CH$_2$F$_2$ and CH$_3$F are based on the number of moles of bis(fluoromethyl)ether charged to the reactor.

TABLE 7

| Temp/°C. | % Yield | | % BFME Conversion | Molar Ratio CH$_2$F$_2$/CH$_3$F |
|---|---|---|---|---|
| | CH$_3$F | CH$_2$F$_2$ | | |
| 229 | 6.41 | 85.85 | 92.26 | 13.40 |
| 258 | 7.36 | 86.72 | 94.08 | 11.78 |
| 296 | 10.16 | 86.34 | 96.51 | 8.49 |
| 320 | 10.68 | 86.30 | 96.98 | 8.76 |
| 364 | 11.97 | 85.90 | 97.87 | 7.18 |
| 400 | 10.692 | 85.68 | 99.13 | 8.01 |

EXAMPLE 10

Heating BFME in Presence of Stainless Steel Grade 304 Mesh and HF

The procedure of example 9 was followed except that the Inconel reactor was packed with 82.8 g (200 cms$^3$) of stainless steel grade 304 mesh, which had not been air-treated. The results are shown in Table 8, in which the yields of CH$_2$F$_2$ and CH$_3$F are based on the number of moles of bis(fluoromethyl)ether charged to the reactor.

TABLE 8

| Temp/°C. | % Yield | | % BFME Conversion | Molar Ratio CH$_2$F$_2$/CH$_3$F |
|---|---|---|---|---|
| | CH$_3$F | CH$_2$F$_2$ | | |
| 295 | 0.28 | 0:30 | 0.58 | 1.05 |
| 336 | 3.94 | 6.91 | 10.85 | 1.75 |
| 369 | 19.34 | 58.61 | 83.15 | 3.03 |
| 395 | 10.05 | 51.51 | 74.85 | 5.12 |

EXAMPLE 11

Heating BFME in Presence of Air-Treated Stainless Steel Grade 316 Rings and HF

The procedure of example 3 was followed except that the Inconel reactor was packed with 133.5 g (200 cms$^3$) of air-treated stainless steel grade 316 rings, and the example was conducted isothermally and the composition of the off-gas monitored at regular intervals. The results are shown in Table 9, in which the yields of $CH_2F_2$ and $CH_3F$ are based on the number of moles of bis(fluoromethyl)ether charged to the reactor.

TABLE 9

| Temp/°C. | % Yield | | % BFME Conversion | Molar Ratio $CH_2F_2/CFH_3$ |
|---|---|---|---|---|
| | $CH_3F$ | $CH_2F_2$ | | |
| 316 | 6.41 | 92.72 | 94.28 | 14.46 |
| 316 | 7.36 | 93.63 | 95.38 | 12.72 |
| 316 | 10.16 | 95.50 | 97.86 | 9.4 |
| 316 | 10.68 | 90.00 | 94.51 | 8.43 |
| 316 | 11.97 | 90.62 | 96.95 | 7.57 |

EXAMPLE 12

Heating BFME in Presence of Stainless Steel Grade 316 Rings and HF

The procedure of example 11 was followed except that the Inconel reactor was packed with 133.5 g (200 cms$^3$) of stainless steel grade 316 mesh, which had not been air-treated. The results are shown in Table 10, in which the yields of $CH_2F_2$ and $CH_3F$ are based on the number of moles of bis(fluoromethyl)ether charged to the reactor.

TABLE 10

| Temp/°C. | % Yield | | % BFME Conversion | Molar Ratio $CH_2F_2/CH_3F$ |
|---|---|---|---|---|
| | $CH_3F$ | $CH_2F_2$ | | |
| 188 | 0.00 | 0.00 | 0.00 | — |
| 231 | 0.31 | 1.71 | 2.03 | 5.5 |
| 266 | 0.66 | 6.97 | 7.63 | 10.6 |
| 295 | 0.96 | 12.94 | 13.91 | 13.5 |
| 325 | 1.53 | 18.57 | 20.10 | 12.1 |
| 339 | 3.17 | 35.06 | 38.24 | 11.1 |
| 357 | 5.23 | 67.06 | 72.77 | 12.8 |
| 367 | 6.75 | 91.45 | 99.22 | 13.5 |

EXAMPLE 13

Heating BFME in Presence of Aluminium Fluoride

Bis(fluoromethyl)ether was vaporised by bubbling nitrogen through liquid bis(fluoromethyl)ether at room temperature at a flow rate of 50 cms$^3$/minute. The vapour was fed to an Inconel tube (length 18 inches and diameter 1 inch) packed with 200 cms$^3$ of aluminium fluoride pellets and the tube was heated from room temperature to an elevated temperature over a period of 5 hours.

Three runs were carried out at various temperatures. The reactor off gas was followed as a function of temperature and the results are shown in Table 11.

TABLE 11

| TEMP/ °C. | % Yield (moles) | | | | | MOLAR RATIO $CH_2F_2/CH_3F$ |
|---|---|---|---|---|---|---|
| | $CH_4$ | $CH_3F$ | $CH_2F_2$ | BFME | Others | |
| 145 | — | 1.15 | 1.15 | 91.7 | 6.0 | 1.0 |
| 340 | — | 3.69 | 3.29 | 48.9 | 44.1 | 0.89 |
| 405 | 3.39 | 21.5 | 19.8 | 35.0 | 20.1 | 0.92 |

EXAMPLE 14

Heating BFME in Presence of Aluminium Fluoride and HF

The procedure of example 3 was followed except that the Inconel tube was packed with 200 cms$^3$ of aluminium fluoride pellets. The results are shown in Table 12, in which the yields of $CH_2F_2$ and $CH_3F$ are based on the number of moles of bis(fluoromethyl)ether charged to the reactor.

TABLE 12

| TEMP/ °C. | % Yield (moles) | | | | | MOLAR RATIO $CH_2F_2/CH_3F$ |
|---|---|---|---|---|---|---|
| | $CH_4$ | $CH_3F$ | $CH_2F_2$ | BFME | Others | |
| 155 | — | 3.06 | 0.08 | 81.6 | 15.1 | 0.03 |
| 257 | 0.05 | 37.9 | 20.12 | 20.2 | 21.6 | 0.53 |
| 343 | 1.5 | 10.5 | 16.2 | 10.4 | 73.5 | 1.54 |
| 398 | 9.2 | 0.4 | 26.2 | 3.6 | 61.0 | 65.5 |

EXAMPLE 15

Heating BFME in Presence of Zinc Impregnated Chromia Catalyst and HF

The procedure of example 3 was followed except that the Inconel tube was packed with 135 g (200 cms$^3$) of zinc impregnated chromia pellets.

The zinc impregnated chromia pellets were prepared by immersing chromia pellets in aqueous zinc chloride so that all surfaces of the chromia were wetted and drying the pellets in air by direct heating.

The results are shown in Table 13, in which the yields of $CH_2F_2$ and $CH_3F$ are based on the number of moles of bis(fluoromethyl)ether charged to the reactor.

TABLE 13

| Temp/°C. | % Yield | | BFME Conversion/% | Molar Ratio $CH_2F_2/CH_3F$ |
|---|---|---|---|---|
| | $CH_3F$ | $CH_2F_2$ | | |
| 172 | 82.42 | 1.39 | 83.81 | 0.02 |
| 192 | 93.96 | 2.14 | 96.11 | 0.02 |
| 218 | 97.58 | 2.09 | 99.67 | 0.02 |
| 267 | 100.00 | 0.00 | 100.0 | 0.00 |
| 193 | 100.00 | 0.00 | 100.0 | 0.00 |
| 160 | 93.85 | 2.85 | 97.65 | 0.03 |

EXAMPLE 16

Heating BFME in Presence of Air-Treated Chromia and HF

The procedure of example 3 was followed except that the Inconel tube was packed with 200 cms$^3$ of air-treated chromia pellets. The results are shown in Table 14, in which the yields of $CH_2F_2$ and $CH_3F$ are based on the number of moles of bis(fluoromethyl)ether charged to the reactor.

TABLE 14

| Temp/°C. | % Yield | | BFME Conversion/% | Molar Ratio $CH_2F_2/CH_3F$ |
|---|---|---|---|---|
| | $CH_3F$ | $CH_2F_2$ | | |
| 174 | 35.5 | 30.9 | 66.4 | 0.87 |
| 216 | 46.6 | 43.3 | 89.9 | 0.98 |

TABLE 14-continued

| Temp/°C. | % Yield CH$_3$F | % Yield CH$_2$F$_2$ | BFME Conversion/% | Molar Ratio CH$_2$F$_2$/CH$_3$F |
|---|---|---|---|---|
| 225 | 44.2 | 48.4 | 92.6 | 1.10 |
| 230 | 43.6 | 48.35 | 92.0 | 1.11 |

EXAMPLE 17

Heating BFME in the Presence of HF-Treated Chromia

Bis(fluoromethyl)ether was Vaporised by bubbling nitrogen through liquid bis(fluoromethyl)ether at room temperature at a flow rate of 75 mls/minute. The vapour was fed to an Inconel tube (length 12 inches and diameter 1 inch) packed with 120 g of chromia pellets which had been pre-treated by heating the pellets to 350° C. for 4 hours in a stream of hydrogen fluoride having a flow rate of 150 ml/minute. The tube was heated from room temperature to elevated temperature and the composition of the reactor off gas was followed (Gas Chromatography) as a function of temperature and the results are shown in Table 15.

TABLE 15

| Temp/°C. | % Yield CH$_3$F | % Yield CH$_2$F$_2$ | BFME Conversion/% | Molar Ratio CH$_2$F$_2$/CH$_3$F |
|---|---|---|---|---|
| 185 | 29.11 | 43.79 | 74.38 | 1.5 |
| 224 | 32.34 | 62.54 | 95.71 | 1.93 |
| 246 | 35.40 | 63.77 | 99.97 | 1.8 |
| 256 | 35.22 | 62.21 | 100.0 | 1.77 |
| 292 | 35.66 | 57.45 | 98.09 | 1.61 |
| 320 | 35.88 | 54.57 | 97.62 | 1.52 |

EXAMPLE 18

Heating BFME in the Presence of Iron (III) Doped Chromia 100 g of chromia pellets were added to an aqueous solution of iron (III) nitrate and the water was then removed by direct heating to give a 2.6% Iron (III) impregnated chromia catalyst. 100 g of the catalyst was charged to an Inconel reactor (length 12 inches and diameter 1 inch) and heated in nitrogen at 300° C. for 28 hours and then pre-fluorinated by heating in hydrogen fluoride at 350° C. for 12 hours. Finally the catalyst was heated in nitrogen at 250° C. for 15 hours.

Bis(fluoromethyl)ether was vaporised by bubbling nitrogen through liquid bis(fluoromethyl)ether at room temperature at a flow rate of 75 mls/minute. The vapour was fed to the Inconel reactor. The tube was heated from room temperature to elevated temperature and the composition of the reactor off gas was followed (Gas Chromatography) as a function of temperature and the results are shown in Table 16.

TABLE 16

| Temp/°C. | % Yield CH$_3$F | % Yield CH$_2$F$_2$ | BFME Conversion/% | Molar Ratio CH$_2$F$_2$/CH$_3$F |
|---|---|---|---|---|
| 232 | 23.32 | 70.72 | 94.27 | 3.03 |
| 250 | 22.59 | 73.92 | 99.87 | 3.27 |
| 265 | 20.89 | 76.36 | 98.93 | 3.66 |
| 272 | 19.15 | 77.24 | 99.63 | 4.03 |
| 288 | 17.65 | 77.10 | 99.79 | 4.37 |
| 300 | 19.34 | 77.80 | 99.45 | 4.02 |

EXAMPLE 19

Heating BFME in the Presence of Iron (II) Doped Chromia 85 g of the Iron (III) doped chromia catalyst prepared as described in example 18 were charged to an Inconel reactor as described in Example 18 and heated in hydrogen at 375° C. to reduce iron (III) to iron. The catalyst was then pre-fluorinated by heating in hydrogen fluoride at 350° C. for 12 hours to oxidise the iron to iron (II).

Bis(fluoromethyl)ether was vaporised by bubbling nitrogen through liquid bis(fluoromethyl)ether at room temperature at a flow rate of 75 mls/minute. The vapour was fed to the Inconel reactor. The tube was heated from room temperature to elevated temperature and the composition of the reactor off gas was followed (Gas Chromatography) as a function of temperature and the results are shown in Table 17.

TABLE 17

| Temp/°C. | % Yield CH$_3$F | % Yield CH$_2$F$_2$ | BFME Conversion/% | Molar Ratio CH$_2$F$_2$/CH$_3$F |
|---|---|---|---|---|
| 235 | 16.09 | 61.86 | 77.95 | 3.84 |
| 256 | 10.51 | 68.70 | 79.22 | 6.54 |
| 270 | 9.23 | 66.58 | 75.81 | 7.21 |

EXAMPLE 20

Heating BFME in the Presence of Nickel Doped Chromia 100 g of chromia pellets were added to a saturated aqueous solution of nickel nitrate and the water was then removed by direct heating to 150° C., to give a 2.7% nickel impregnated chromia catalyst. 100 g of the catalyst was charged to an Inconel reactor (length 12 inches and diameter 1 inch) and heated in nitrogen at 300° C. for 28 hours and then pre-fluorinated by heating in hydrogen fluoride at 350° C. for 4 hours. Finally the catalyst was heated in nitrogen at 250° C. for 15 hours.

Bis(fluoromethyl)ether was vaporised by bubbling nitrogen through liquid bis(fluoromethyl)ether at room temperature at a flow rate of 75 mls/minute. The vapour was fed to the Inconel reactor. The tube was heated from room temperature to elevated temperature and the composition of the reactor off gas was followed (Gas Chromatography) as a function of temperature and the results are shown in Table 18.

TABLE 18

| Temp/°C. | % Yield CH$_3$F | % Yield CH$_2$F$_2$ | BFME Conversion/% | Molar Ratio CH$_2$F$_2$/CH$_3$F |
| --- | --- | --- | --- | --- |
| 223 | 36.78 | 60.35 | 97.14 | 1.64 |
| 234 | 28.25 | 69.10 | 97.35 | 2.45 |
| 241 | 21.60 | 77.56 | 99.16 | 3.6 |
| 251 | 23.42 | 73.27 | 97.82 | 3.13 |
| 265 | 26.48 | 71.64 | 98.12 | 2.7 |
| 279 | 24.45 | 72.35 | 99.53 | 3.0 |

EXAMPLE 21

Heating BFME in the Presence of Mixed Iron Oxide/Chromia 112.7 g of a catalyst comprising 9:1 by weight iron (III) oxide and chromia was charged to an Inconel reactor (length 12 inches and diameter 1 inch) and heated in hydrogen fluoride at 300° C. for 12 hours. The catalyst was then heated in nitrogen at 230° C. for 15 hours.

Bis(fluoromethyl)ether was vaporised by bubbling nitrogen through liquid bis(fluoromethyl)ether at room temperature at a flow rate of 75 mls/minute. The vapour was fed to the Inconel reactor. The tube was heated from room temperature to elevated temperature and the composition of the reactor off gas was followed (Gas Chromatography) as a function of temperature and the results are shown in Table 19.

TABLE 19

| Temp/°C. | % Yield CH$_3$F | % Yield CH$_2$F$_2$ | BFME Conversion/% | Molar Ratio CH$_2$F$_2$/CH$_3$F |
| --- | --- | --- | --- | --- |
| 223 | 23.34 | 73.52 | 99.15 | 3.15 |
| 235 | 19.33 | 68.41 | 87.75 | 3.54 |

EXAMPLE 22

Heating BFME in the Presence of Pre-Fluorinated Aluminium Fluoride 103.9 g of aluminium fluoride was charged to an Inconel reactor (length 12 inches and diameter 1 inch), heated in nitrogen at 300° C. for 4 hours and then heated in hydrogen fluoride at 300° C. for 12 hours. The catalyst was then heated in nitrogen at 240° C. for 16 hours.

Bis(fluoromethyl)ether was vaporised by bubbling nitrogen through liquid bis(fluoromethyl)ether at room temperature at a flow rate of 75 mls/minute. The vapour was fed to the Inconel reactor. The tube was heated from room temperature to elevated temperature and the composition of the reactor off gas was followed (Gas Chromatography) as a function of temperature and the results are shown in Table 20.

TABLE 20

| Temp/°C. | % Yield CH$_3$F | % Yield CH$_2$F$_2$ | BFME Conversion/% | Molar Ratio CH$_2$F$_2$/CH$_3$F |
| --- | --- | --- | --- | --- |
| 235 | 30.46 | 68.5 | 98.96 | 2.25 |

EXAMPLE 23

Heating BFME in the Presence of Chromia and Hydrogen Fluoride at Elevated Pressure Bis(fluoromethyl)ether was vaporised by bubbling nitrogen through liquid bis(fluoromethyl)ether at room temperature at a flow rate of 75 mls/minute. The vapour was fed to an Inconel tube (diameter 0.37 inch) packed with 15 mls of chromia pellets. Hydrogen fluoride was also fed to the reactor at a flow rate of 0.038 g/minute by passing 44 mls/minute of nitrogen through a bomb containing liquid hydrogen fluoride. The reactor was pressurised to 15 barg.

The tube was heated from room temperature to elevated temperature and the composition of the reactor off gas was followed (Gas Chromatography) as a function of temperature and the results are shown in Table 21.

TABLE 21

| Temp/°C. | % Yield CH$_3$F | % Yield CH$_2$F$_2$ | BFME Conversion/% | Molar Ratio CH$_2$F$_2$/CH$_3$F |
| --- | --- | --- | --- | --- |
| 240 | 39.0 | 29.6 | 95.0 | 0.76 |

EXAMPLES 24 TO 29

In the following examples, 1 ml of the catalyst in a finely divided form was charged to a 0.5 mm internal diameter stainless steel reactor tube and bis(fluoromethyl)ether was pumped through a vaporiser to give a bis(fluoromethyl)ether vapour feed with a flow rate of 5 ml/minute. This stream was mixed with 10 ml/minute nitrogen and the mixed stream passed over the catalyst at the temperature given in Table 22. The reactor off gas was analysed by gas chromatography and the results are shown in Table 22.

TABLE 22

| EXAMPLE | CATALYST | TEMP °C. | % Yield CH$_2$F$_2$ | % Yield CH$_3$F |
| --- | --- | --- | --- | --- |
| 24 | HgF$_2$ | 400 | 40 | N/D |
| 25 | LaF$_3$ | 350 | 84 | N/D |
| 26 | SnF$_2$ | 450 | N/D | 4 |
| 27 | MnF$_3$ | 240 | 23 | N/D |
| 28 | CrF$_3$ | 200 | 50 | 25 |
| 29 | FeF$_3$ | 340 | 11 | N/D |

EXAMPLE 30

1 g of CaF$_2$ was charged to an Inconel reactor heated at 240° C. Hydrogen fluoride was passed over the catalyst for 15 minutes at 4.5 ml/minute after which a bis(fluoromethyl)ether feed (1.5 ml/minute) was also passed over the catalyst. The temperature was increased to 350° C. and the reactor off-gases were analysed by gas chromatography. Analysis showed that the gases comprised 90% bis(fluoromethyl)ether, 9.5% CH$_2$F$_2$, and 0.5% CH$_3$F.

EXAMPLE 31

Formaldehyde monomer, generated by heating paraformaldehyde was fed at 80 cm$^3$/minute on a stream of nitrogen (400 cms$^3$/minute) to an Inconel reactor tube charged with a catalyst comprising CsF supported on charcoal, whilst co-feeding hydrogen fluoride at 1000 cm$^3$/minute. The reactor tube was heated to 300° C. The reactor off-gases were scrubbed to remove hydrogen fluoride and analysed by gas chromatography. The reactor off-gases comprised 48.5% bis(fluoromethyl)ether.

We claim:

1. A process for the production of a bis(fluoromethyl)ether composition suitable for use in the production of difluoromethane which comprises contacting formaldehyde with hydrogen fluoride either (i) in the liquid phase or (ii) in the presence of a catalyst in the vapor phase to form a composition comprising bis(fluoromethyl)ether and an equimolar amount of by-product water relative to the bis(fluoromethyl)ether, separating at least part of the by-product water from the composition and recovering a bis(fluoromethyl)ether composition containing less than an equimolar amount of water relative to the bis(fluoromethyl)ether.

2. A process for the production of a bis(fluoromethyl)ether composition suitable for use in the production of difluoromethane according to claim 1 which comprises contacting formaldehyde with liquid hydrogen fluoride to form a composition comprising bis(fluoromethyl)ether and an equimolar amount of by-product water relative to the bis(fluoromethyl)ether, separating at least part of the by-product water from the composition and recovering a bis(fluoromethyl)ether composition in which the mole ratio of bis(fluoromethyl)ether to water is at least 2:1.

3. A process for the production of a bis(fluoromethyl)ether composition suitable for use in the production of difluoromethane according to claim 1 which comprises contacting formaldehyde with hydrogen fluoride in the vapor phase in the presence of a catalyst form a composition comprising bis(fluoromethyl)ether and an equimolar amount of by-product water relative to the bis(fluoromethyl)ether, separating at least part of the by-product water from the composition and recovering a bis(fluoromethyl)ether composition in which the mole ratio of bis(fluoromethyl)ether to water is at least 2:1.

4. A process as claimed in claim 2 wherein the recovered composition comprises at least 20 mole % of bis(fluoromethyl)ether.

5. A process as claimed in claim 3 wherein the recovered composition comprises at least 20 mole % of bis(fluoromethyl)ether.

6. A process as claimed in claim 1, 2 or 3, wherein water is continually separated from the bis(fluoromethyl)ether.

7. A process as claimed in claim 1, 2 or 3, wherein the separation of by-product water is effected by removing bis(fluoromethyl)ether from the as-formed composition.

8. A process as claimed in claim 1, 2 or 3, wherein the recovered bis(fluoromethyl)ether composition is suitable for the production of difluoromethane in a yield of greater than 20% based on the bis(fluoromethyl)ether in the composition.

* * * * *